(12) United States Patent
Vinson et al.

(10) Patent No.: US 8,383,108 B2
(45) Date of Patent: *Feb. 26, 2013

(54) THERAPEUTIC USES OF MONOCLONAL ANTIBODIES TO THE ANGIOTENSIN-II TYPE 1 RECEPTOR

(75) Inventors: Gavin Paul Vinson, London (GB); John Richard Puddefoot, London (GB); Stewart Barker, London (GB)

(73) Assignee: Queen Mary & Westfield College, University of London, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/087,770

(22) Filed: Apr. 15, 2011

(65) Prior Publication Data

US 2011/0256139 A1 Oct. 20, 2011

Related U.S. Application Data

(63) Continuation of application No. 10/525,277, filed as application No. PCT/GB03/03758 on Aug. 21, 2003, now Pat. No. 7,951,904.

(30) Foreign Application Priority Data

Aug. 21, 2002 (GB) .................................. 0219524.6

(51) Int. Cl.
*A61K 39/395* (2006.01)
*A61K 35/12* (2006.01)
(52) U.S. Cl. ............... 424/130.1; 424/141.1; 424/155.1; 424/277.1
(58) Field of Classification Search .................. None
See application file for complete search history.

(56) References Cited

U.S. PATENT DOCUMENTS

| 6,063,620 A | 5/2000 | Vinson et al. |
| 2000/6003483 | 2/2006 | Barker et al. |

FOREIGN PATENT DOCUMENTS

| CA | 2093495 A1 | 4/1993 |
| CN | 1141000 | 1/1997 |
| WO | 95/09186 | 4/1995 |
| WO | 95/12410 | 5/1995 |
| WO | 02/061087 A2 | 8/2002 |
| WO | WO 02061087 * | 8/2002 |
| WO | 2004/018519 A2 | 3/2004 |

OTHER PUBLICATIONS

Colman et al, Research in Immunology, 1994; 145(1): 33-36.*
Abaza et al (Journal of Protein Chemistry, vol. 11, No. 5, 1992, pp. 433-444.*
Tamarat, R., et al., Angiotensin II angiogenic effect in vivo involves vascular endothelial growth factor- and inflammation-related pathways, Lab Invest. Jun. 2002;82(6):747-56.
Fujimoto, Y., et al., Angiotension II Type 1 Receptor in Human Pancreatic Cancer and Growth Inhibition by Angiotension II Type 1 Receptor Antagonist, FEBS Letters, 2001;495:197-200.
Sequence Search Result—Vinson, 2010.
Sequence Search Result—Burmer, 2010.
Humphries, et al., Conjugation of synthetic peptides to carrier proteins for cell adhesion studies, J. of Tissue Culture Methods, 1994;16:239-242.
Ezzell, Cancer "Vaccines": An Idea Whose Time Has Come?, J. NIH Res., 1995;7:46-49.
Spitler, L. E., Cancer vaccines: the interferon analogy, Cancer Biother. 1995 Spring;10(1):1-3.
Boon, T., Toward a genetic analysis of tumor rejection antigens, Adv Cancer Res. 1992;58:177-210.
Degruijl, T. D., et al., Cancer vaccine strategies get bigger and better, Nat Med. Oct. 1999;5(10):1124-5.
Barker, et al., "Monoclonal antibody to a conserved sequence in the extracellular domain recognizes the angiotensin II ATi receptor in mammalian target tissues," /. of Molecular Endocrinology (1993) 11:241-245.
Cheng, et al., "Young SHR express increased type 1 angiotensin II receptors in renal proximal tubule," Am ] Physiol. (1998) 274(1 Pt 2):F10-7.
De Paepe, et al., "Growth stimulatory angiotensin II type-1 receptor is upregulated in breast hyperplasia and in situ carcinoma but not in invasive carcinoma," Histochem Cell Biol(2001) 116:247-254.
Harrison-Bernard, et al., "Immunohistochemical localization of ANG II ATi receptor in adult rat kidney using a monoclonal antibody," Am J Physiol. (1997) 273(1 Pt 2):F170-7.
Inwang, et al., "Angiotensin II type 1 receptor expression in human breast tissues," /. of Cancer (1997) 75 (9):1279-1283.
Kapas, et al., "Internalization of the type I angiotensin 11 receptor (ATI) is required for protein kinase C activation but not for inositol triphosphate release in the angiotensin II stimulated rat adrenal zonaglomerulosa cell," Biochemical and Biophysical Research Communications (1994) 204(3):1292-1298.
Ling, et al., "Matrix-dependent gene expression of Egr-1 and PDGF a regulate angiotensin II-induced proliferation in human vascular smooth muscle cells," Hypertension (1999) 34:1141-1146.
Marsigliate, et al.,, "ATI angiotensin II receptor subtype in the human larynx and squamous laryngeal carcinoma," Cancer (1996) 110:19-27.
Murphy, et al., "Isolation of a cDNA encoding the vascular type-1 angiotensin II receptor," Nature (1991) 351:233-236.
Richards, et al., "Inhibition of central angiotensin responses by angiotensin type-1 receptor antibody," Hypertension (1993) 21(6):1062-1065.
Tahmasebi, et al., "Transcription of the prorenin gene in normal and diseased breast," European ]. of Cancer (1998) 34(11):1777-1782.
Touyz, et al., ouyz et al., "Angiotensin II stimulates DNA and protein synthesis ihViulaQQfiotth muscle cells from human arteries: role of extracellular signal-regulated kinases," Hypertension (1999) 17:907-916.

(Continued)

*Primary Examiner* — Lei Yao
(74) *Attorney, Agent, or Firm* — Pepper Hamilton, LLP

(57) ABSTRACT

The use of monoclonal antibodies to the angiotensin-II type-I receptor is provided for the treatment of cancer and vascular smooth muscle cell proliferation. Specifically, use is provided of a monoclonal antibody or a fragment thereof to a peptide comprising the N-terminal portion of the angiotensin-II type-1 receptor defined by the sequence MILNSSTEDG IKRIQDDCPK AGHRHNYIFVM IPTLYSIIFV VGIFG in the preparation of a medicament for the treatment of cancer or in the preparation of a medicament for the treatment of vascular smooth muscle (VSM) cell proliferation.

4 Claims, 6 Drawing Sheets

OTHER PUBLICATIONS

Vinson, et al., "Internalisation of the type I angiotensin II receptor (ATI) and angiotensin II function in the rat adrenal zonaglomerulose cell," /. of Endocrinology (1994) 141:R5-R9.

Yang, et al., "Involvement of MAP kinase in angiotension H-induced phosphorylation and intracellular targeting of neuronal ATi receptors," /. of Neuroscience(1997) 17(5):1660-1669.

Yang, et al., "Increased angiotensin II type 1 receptor expression in hypercholesterolemicatherosclerosis in rabbits," ArteriosderThromb Vase Bwl. (1998) 18(9):1433-9.

International Search Report dated Apr. 21, 2004 for International Application No. PCT/GB03/03758.

Ngo, et al., in The Protein Folding Problem and Tertiary Structure Prediction, 1994, Merz, et al., (ed.), Birkhauser, Boston, MA, pp. 433 and 492-495.

Burgess, W. H., et al., Possible dissociation of the heparin-binding and mitogenic activities of heparin-binding (acidic fibroblast) growth factor-1 from its receptor-binding activities by site-directed mutagenesis of a single lysine residue, J Cell Biol. Nov. 1990;111(5 Pt 1):2129-38.

Lazar, E. et al., Transforming growth factor alpha: mutation of aspartic acid 47 and leucine 48 results in different biological activities, Mol Cell Biol. Mar. 1988;8(3):1247-52.

Colman, et al., Effects of amino acid sequence changes on antibody-antigen interactions, Research in Immunology, 1995;145(1):33-36.

Abaza, et al., Effects of amino acid substitutions outside an antigenic site on protein binding to monoclonal antibodies of predetermined specificity obtained by peptide immunization: demonstration with region 94-100 (antigenic site 3) of myoglobin, Journal of Protein Chemistry, 1995;11(5):433-444.

Notice of Allowance dated Jan. 20, 2011 in related U.S. Appl. No. 10/525,277.

Final Office Action dated Nov. 9, 2010 in related U.S. Appl. No. 10/525,277.

Office Action dated May 21, 2010 in related U.S. Appl. No. 10/525,277.

Office Action dated Nov. 25, 2009 in related U.S. Appl. No. 10/525,277.

Notice of Allowance dated Jun. 25, 2009 in related U.S. Appl. No. 10/525,277.

Office Action dated Dec. 4, 2008 in related U.S. Appl. No. 10/525,277.

Office Action dated Jul. 3, 2012 in related U.S. Appl. No. 12/867,911.

Fukuda, N., et al., MolBi-4 Regulation of growth capability and TGF-_receptor expression due to angiotensin II Type 1 and Type II receptors in vascular smooth muscle cells, Japanese Journal of Clinical Physiology, 2000;30, supplement:115.

Muscella, A., et al., Angiotensin II AT1 receptors and Na+/K+ ATPase in human umbilical vein endothelial cells, J Endocrinol. Dec. 1997;155(3):587-93.

Ishida, J., et al., [Angiotensin II and apoptosis], Nihon Rinsho. May 1999;57(5):1117-23.

Rodondo-Muller, M. A., et al., Anti-cancer actions of a recombinant antibody (R6313/G2) against the angiotensin II AT1 receptor, Endocr Relat Cancer. Mar. 2008;15(1):277-88.

* cited by examiner

```
Human     AT1       MILNSST EDGIKRIQDD CPKAGRHNYIFVMIPTLYSIIFVVGIFG
Chimp     AT1       ------- ---------- ----------------------------
Murine    AT1b      ------- ---------- ----------------------------
Bovine    AT1       ------- ---------- -----------I----------------
Canine    AT1       ------- ---------- ----------------------------
Ovine     AT1       ------- ---------- -----------I------------L---
Rabbit    AT1       -M----- ---------- ----------------------------
Rat       AT1b      ------- ---------- -----------------------M----
Guinea pig AT1      ------- Q--------- ---X---S--------------------
Rat       AT1a      -X----X D--------- -------S--------------------
Mouse     AT1a      -X----X ---------- --XS---S-------------M------
Gerbil    AT1       -X----X D--------- -------S--------------------
```

- denotes identical residue

X denotes missing residue

FIG. 9

THERAPEUTIC USES OF MONOCLONAL ANTIBODIES TO THE ANGIOTENSIN-II TYPE 1 RECEPTOR

CROSS-REFERENCE TO RELATED APPLICATIONS

This application is a continuation of U.S. Ser. No. 10/525,277 filed Feb. 22, 2005, now U.S. Pat. No. 7,951,904, which is the U.S. National Stage filing of International Application Serial No. PCT/GB2003/003758 filed Aug. 21, 2003, which claims priority to GB 0219524.6 filed Aug. 21, 2002, each of which is incorporated herein by reference in its entirety.

FIELD OF THE INVENTION

The present invention relates to therapeutic uses of monoclonal antibodies to the angiotensin-II type-I receptor, in particular in the treatment of cancer and vascular smooth muscle cell proliferation.

BACKGROUND OF THE INVENTION

Angiotensin-II plays a central role in mammalian electrolyte homeostasis and blood pressure control (Peach *Physiol. Rev* 57 313-370 (1977); Vinson et al "*The Adrenal Cortex*", Prentice Hall, Englefield Heights (1992)). Two main types of angiotensin-II receptors, designated types 1 and 2 (AT1 and AT2), have been recognised, but the majority of the well known actions of angiotensin-II occur via the AT1 subtype (Herblin et al *Am. J. Hypertens.* 4 299S-302S (1991); Ouali et al *J. Steroid. Biochem. Mol. Biol.* 43 271-280 (1992)).

A monoclonal antibody 6313/G2 to the AT1 receptor subtype (Barker et al *J. Mol. Endocrinol.* 11 241-245 (1993)) has been used to study the distribution of the receptor (Vinson et al *Mol. Med. Today* 1 35-38 (1995)). The monoclonal antibody has been suggested for use as a therapeutic agent to control vaso-constriction, for example in the treatment of hypertension or uterine contractions.

The antibody has been used as a specific imaging agent in various tissues, for example laryngeal cancer (Marsigliante et al *Cancer Letters* 110 19-27 (1996)), kidney (Harrison-Bernard et al *Am. J. Physiol.* 42 F170-F177 (1997); Cheng et al *Am. J. Physiol.* 43 F10-F17 (1998)), and brain (Yang et al *J. Neuroscience* 17 1660-1669 (1997)). The antibody has been shown to block angiotensin-II induced AT1 receptor internalisation and PKC activation but conversely promotes the calcium response (Kapas et al *Biochem. Biophys. Res. Comm.* 204 1292-1298 (1994; Vinson et al *J. Endocrinol.* 141 R5-R9 (1994)). The presence of AT1 and At2 receptors in breast tumours has been reported with local production of angiotensin (Inwang et al *Brit. J. Cancer* 75 1279-1283 (1997); Tahmasebi et al *Eur. J. Cancer* 34 1777-1782 (1998)).

Monoclonal antibody 6313/G2 is secreted by a hybridoma cell line deposited on 21 Jul. 1993 with the European Collection of Animal Cell Cultures (ECACC), Porton Down, United Kingdom, under the Budapest Treaty, and designated by the accession no. 93072117. The deposit was made by Dr Gavin P Vinson and Dr Stewart Barker, Department of Biochemistry, Queen Mary & Westfield College, Mile End Road, London E1 4NS. The depositor has authorised the applicant to refer to the deposited material in the application and has given his unreserved and irrevocable consent to the deposited material being made available to the public in accordance with Rule 28(1)(d) of the European Patent Convention.

The hybridoma cell line produces an antibody that specifically binds to amino acid residues 8 to 17 of the rat vascular smooth muscle AT1 receptor, which sequence is also found in the AT1 receptor of human and bovine cells. The epitope sequence is as follows:

EDGIKRIQDD (SEQ ID NO:2)

Or, alternatively expressed as,

NH$_2$-Glu-Asp-Gly-Ile-Lys-Arg-Ile-Gln-Asp-Asp-COOH

It has now been surprisingly found that monoclonal antibodies to the peptide sequence comprising the N-terminal sequence of the angiotensin-II type-1 receptor have additional therapeutic uses in certain medical conditions where such uses were not previously suggested or shown. Furthermore, these therapeutic effects are seen in the ability of the monoclonal antibodies to block the harmful actions of angiotensin-II in the medical conditions concerned whilst preserving the beneficial actions of the molecule. A functionally important role for the entire N-terminal sequence has now been realised.

SUMMARY OF THE INVENTION

According to a first aspect of the invention, there is provided the use of a monoclonal antibody or a fragment thereof to a peptide comprising the N-terminal portion of the angiotensin-II type-1 receptor defined by the sequence MILNSSTEDG IKRIQDDCPK AGRHNYIFVM IPTLYSIIFV VGIFG (SEQ ID NO:1) or a fragment thereof, in the preparation of a medicament for the treatment of cancer.

BRIEF DESCRIPTION OF THE DRAWINGS

The invention will now be further described by way of reference to the following Figures which are provided for the purposes of illustration only and are not to be construed as being limiting on the invention. Reference is made to a number of Figures in which:

FIG. 9 shows sequence homologies for the N-terminal sequences of angiotensin-11 type-1 receptor from different species, where "X" denotes a missing residue, and "-" denotes an identical residue.

DESCRIPTION OF EMBODIMENTS

Figure 1:
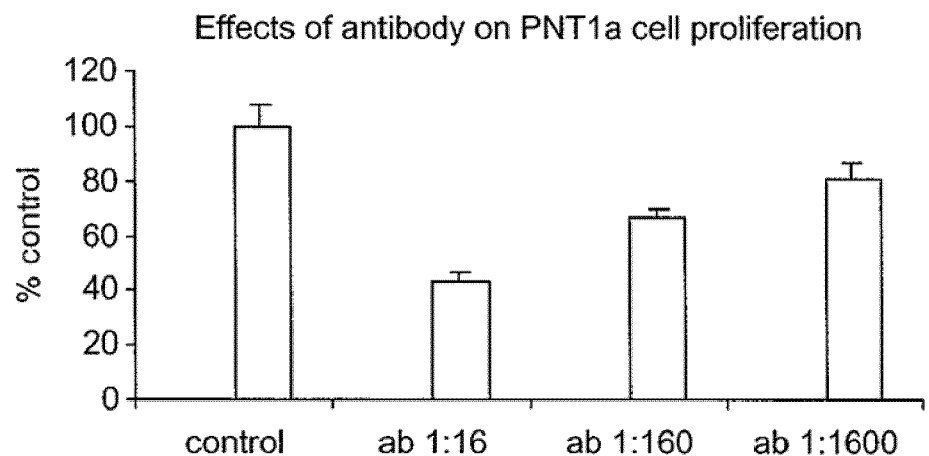
FIG. 1 shows the effects of antibody on PNT1a cell proliferation.

In the above, and throughout this specification, the amino acid residues are designated by the usual IUPAC single letter nomenclature. The single letter designations may be correlated with the classical three letter designations of amino acid residues as follows:

| | | | |
|---|---|---|---|
| A = Ala | G = Gly | M = Met | S = Ser |
| C = Cys | H = His | N = Asn | T = Thr |
| D = Asp | I = Ile | P = Pro | V = Val |
| E = Glu | K = Lys | Q = Gln | W = Trp |
| F = Phe | L = Leu | R = Arg | Y = Tyr |

As used herein, the term "peptide" includes oligopeptide or polypeptide and these terms may be used interchangeably.

The peptide will be of at least the minimum size necessary to confer antigenicity: usually it will be of at least six or seven residues, but may be of any suitable length up to, for example, 20 amino acid residues. Preferably, it may be or nine or ten residues. The best peptides may be expected to correspond to topographical surface features of the natural angiotensin-II type-1 receptor molecule, that is to say those features having some three-dimensional feature protruding from or extending into the ambient surface level of the receptor. Preferred peptides correspond to the region 1 to 45, preferably residues 8 to 17.

Probably the most simple way of ensuring that at least part of the molecule is antigenically equivalent to the peptide is for that part of the molecule to comprise a sequence of amino acid residues which is identical to or conformationally similar to the peptide. However, any other way of producing antigenic equivalence may be used: an example is to use an anti-idiotype antibody or other (even non-proteinaceous) analogue.

The invention therefore encompasses the use of monoclonal antibodies against short peptides (preferably of 10 amino acid residues or fewer, but generally of at least 4 or 5 amino acid residues, for example 6 to 8 residues, or 7 to 9 residues) sharing structural homology with the angiotensin-II type-1 receptor.

In a preferred embodiment, the invention therefore encompasses the use of a monoclonal antibody against a peptide sequence comprising the amino acid sequence:

EDGIKRIQDD or an active fragment thereof and/or conservative mutant thereof. This sequence is taken from rat angiotensin-II type-1 receptor sequence, residues 8 to 17. Conservative substitutions in this fragment would be D for E, E for D, A for G, L or I, R for K, K for R, N for Q, or any combination of these.

The sequence EDGIKRIQDD is fully 100% conserved between the species human, chimpanzee, murine (AT1b) and (AT1b), bovine, canine, ovine, rabbit, and rat (AT1b). Variations are seen in residue 8 for guinea pig which has Q, rat (AT1a) which has D and gerbil which has D. The sequence homologies for these species for the full region 1 to 45 of the N-terminal sequence are shown in FIG. 9.

Accordingly, a preferred consensus sequence for the peptide corresponding to residues 8 to 17 of the angiotensin-II type-1 receptor has the structure:

EDGIKRIQDD where the following residues may each independently be as follows: residue 8 may be E, D or Q, residue 9 may be D or E, residue 10 may be G or A, residue 11 may be I or A, residue 12 may be K or R, residue 13 may be R or K, residue 14 may be I or A, residue 15 may be Q or N, and residues 16 and 17 may each either be D or E.

The peptide will generally be antigenic and capable of stimulating the production of antibodies which, when administered can be used in the treatment of cancer.

As stated above, an active subfragment of the specified sequence may be used as defined. Active subfragments may consist of or include pentapeptides, including one or more of:

```
TEDGI  (SEQ ID NO: 3)
EDGIK  (SEQ ID NO: 4)
DGIKR  (SEQ ID NO: 5)
GIKRI  (SEQ ID NO: 6)
IKRIQ  (SEQ ID NO: 7)
KRIQD  (SEQ ID NO: 8)
RIQDD  (SEQ ID NO: 9)
IQDDC  (SEQ ID NO: 10)
```

Active subfragments may also consist of or include hexapeptides, including one or more of:

```
STEDGI  (SEQ ID NO: 11)
TEDGIK  (SEQ ID NO: 12)
EDGIKR  (SEQ ID NO: 13)
DGIKRI  (SEQ ID NO: 14)
GIKRIQ  (SEQ ID NO: 15)
IKRIQD  (SEQ ID NO: 16)
KRIQDD  (SEQ ID NO: 17)
RIQDDC  (SEQ ID NO: 18)
IQDDCP  (SEQ ID NO: 19)
```

Active subfragments may alternatively consist of or include heptapeptides, including one or more of:

```
SSTEDGI  (SEQ ID NO: 20)
STEDGIK  (SEQ ID NO: 21)
TEDGIKR  (SEQ ID NO: 22)
EDGIKRI  (SEQ ID NO: 23)
DGIKRIQ  (SEQ ID NO: 24)
GIKRIQD  (SEQ ID NO: 25)
IKRIQDD  (SEQ ID NO: 26)
KRIQDDC  (SEQ ID NO: 27)
RIQDDCP  (SEQ ID NO: 28)
IQDDCPK  (SEQ ID NO: 29)
```

Further, active subfragments may consist of or include octapeptides, including:

```
NSSTEDGI  (SEQ ID NO: 30)
SSTEDGIK  (SEQ ID NO: 31)
STEDGIKR  (SEQ ID NO: 32)
TEDGIKRI  (SEQ ID NO: 33)
EDGIKRIQ  (SEQ ID NO: 34)
DGIKRIQD  (SEQ ID NO: 35)
```

```
         GIKRIQDD (SEQ ID NO: 36)

IKRIQDDC (SEQ ID NO: 37)

KRIQDDCP (SEQ ID NO: 38)

RIQDDCPK (SEQ ID NO: 39)

IQDDCPKA (SEQ ID NO: 40)
```

Further, active subfragments may consist of or include nonapeptides, including:

```
         LNSSTEDGI (SEQ ID NO: 41)

NSSTEDGIK (SEQ ID NO: 42)

SSTEDGIKR (SEQ ID NO: 43)

STEDGIKRI (SEQ ID NO: 44)

TEDGIKRIQ (SEQ ID NO: 45)

EDGIKRIQD (SEQ ID NO: 46)

DGIKRIQDD (SEQ ID NO: 47)

GIKRIQDDC (SEQ ID NO: 48)

IKRIQDDCP (SEQ ID NO: 49)

KRIQDDCPK (SEQ ID NO: 50)

RIQDDCPKA (SEQ ID NO: 51)

IQDDCPKAG (SEQ ID NO: 52)
```

Further, active subfragments may consist of or include decapeptides, including:

```
         ILNSSTEDGI (SEQ ID NO: 53)

LNSSTEDGIK (SEQ ID NO: 54)

NSSTEDGIKR (SEQ ID NO: 55)

SSTEDGIKRI (SEQ ID NO: 56)

STEDGIKRIQ (SEQ ID NO: 57)

TEDGIKRIQD (SEQ ID NO: 58)

EDGIKRIQDD (SEQ ID NO: 59)

DGIKRIQDDC (SEQ ID NO: 60)

GIKRIQDDCP (SEQ ID NO: 61)

IKRIQDDCPK (SEQ ID NO: 62)

KRIQDDCPKA (SEQ ID NO: 63)

RIQDDCPKAG (SEQ ID NO: 64)

IQDDCPKAGR (SEQ ID NO: 65)
```

Preferred fragments include those containing some, for example at least four residues of the sequence EDG-IKRIQDD.

It should be noted that combinations of more than one of the above sequences may be used.

Peptides and other molecules used to prepare monoclonal antibodies for use in accordance with the invention may be rendered antigenic, or presented, in a variety of ways. For preference, an antigenic region (such as a peptide fragment or sub-fragment) in a molecule in accordance with the invention will contain the amino acid sequence of choice linked to a carrier peptide or protein. It is generally preferred to have a plurality, for example 5 to 10, copies of a peptide sequence (for example one or more of the above sequences) linked to the carrier. The carrier can for convenience be a generally large protein, which is inert in material respects, and which is derived from a different species or genus from that associated with the natural growth hormone. Examples of carriers include albumins such as human serum albumin, bovine serum albumin and ovalbumin (although not so many peptides will probably be able to be carried in this last case). Alternatively, keyhole limpet haemocyanin can be used. The carrier will generally preferably come from a different species from that on which the fragment is based.

It is not essential that peptide sequences as described above be linked to albumins: they may be linked to other macromolecules, such as β-galactosidase, especially of bacterial origin.

The invention encompasses the use of monoclonal antibodies to molecules being peptides or having peptide regions which share substantial (e.g. greater than 30%, 50% or even 70%, suitably, 80%, 85%, 90% or 95%) sequence homology with the above peptides. Similarly, conservative amino acid substitutions may not decrease the immunogenicity or antigenicity of peptides. Thus antigenically similar homologues will elicit antibody which binds to angiotensin-II type-1 receptors in the same region as the above peptides define. It is well known that the use of homologues can be a means of circumventing "self" tolerance. Thus the use of the corresponding sequences from other species may be advantageous in this invention.

It is alternatively possible for monoclonal antibodies to be prepared against molecules which are or which comprise peptides to be or to include polymers of sequences as described above. Appropriate sequences can be polymerised either by cross-linking of two cysteine residues to form disulphide bonds or by using external chemical coupling agents (such as carbodiimide, glutaraldehyde or other dialdehydes or di- (or poly-) functional carboxylic acids. As a further alternative, recombinant DNA techniques could be used to produce a peptide polymer.

It should be noted that the chemical coupling (which could for example take place through the agency of lysine residues) and disulphide bond formation are not limited to when the coupling residues are at the end of the sequence: internal residues could also be appropriate. Coupling residues, for example cysteine residues, may be added as desired.

It may be found that it is not necessary to couple any of the sequences described above with external peptides. They may be antigenic on their own. In such a case, it may be advisable to select particular adjuvants such as DEAE dextran and Merck 7426.

The monoclonal antibodies for used according to the present invention can be prepared by immunising inbred mice by the standard technique of Kohler & Milstein (*Nature* 256 495-497 (1975)). A peptide corresponding to the epitope sequences described above can be synthesised by any convenient chemical or biological route which is then conjugated to bovine serum albumin (BSA), or another suitable molecule, and then used to immunise the mice. Following a booster injection of the peptide-BSA conjugate, the spleens of the mice are removed, and the splenocytes combined with mouse myeloma cells. Mixed myeloma-lymphocyte hybrids can then be selected by growth in hypoxanthine, thymidine and aminopterin in an appropriate cell culture medium to inhibit proliferation of non-fused myeloma cells and myeloma hybrids.

The hybridoma cells can be screened by ELISA for reactivity against the epitope used of the angiotensin-II type-1 receptor by adaptations of the technique described in Engvall et al *Immunochem.* 8 871 (1991). Alternatively, the antibody capture technique described in Beckmann et al *J. Immunol.* 144 4212 (1990) may be used. Positive hybridoma cells can be injected intraperitoneally into syngeneic Balb/c mice to produce ascites containing high concentrations of monoclonal antibodies raised against the epitope used from the angiotensin-II type-1 receptor N-terminal sequence described above. Alternatively, hybridoma cells can be grown in vitro in flasks or roller bottles by various techniques. Monoclonal antibodies produced in mouse ascites can be purified by ammonium sulphate precipitation, followed by gel exclusion chromatography. Alternatively, affinity chromatography based upon binding of antibody to protein A or protein G can be used, as can affinity chromatography based upon binding to the epitope used to generate the monoclonal antibody. The monoclonal antibody 6313/G2 was prepared as described in Barker et al *J. Mol. Endocrinol.* 11 241-245 (1993). Uses of the antibody in the treatment of hypertension and in controlling uterine contractions were described in WO-A-9509186. However, there was no suggestion of any broader utility in other potential therapeutic areas.

The angiotensin-II type-1 receptor of the rat is described in Murphy et al *Nature* 351 233-236 (1992) and the extracellular domain identified as containing at least residues 8 to 17 is represented by the amino acid sequence

EDGIKRIQDD (SEQ ID NO:2)

The epitopes from the N-terminal sequence residues 1 to 45, preferably 8 to 17, of the angiotensin-II type-1 receptor described above may be varied modified by amino acid substitution, and/or insertion, and/or deletion such that the overall shape and/or conformation of the epitope is still antigenic.

In preferred embodiments of the invention, the monoclonal antibody is 6313/G2. Monoclonal antibody 6313/G2 is secreted by a hybridoma cell line deposited on 21 Jul. 1993 with the European Collection of Animal Cell Cultures (ECACC), Porton Down, United Kingdom, under the Budapest Treaty, and designated by the accession no. 93072117. The hybridoma cell line can suitably be cultured under standard conditions.

In uses of the present invention, the treatment of cancer can include, but is not limited to, inhibition of metastasis, inhibition of binding to matrix proteins of tumour cells, inhibition of invasion by tumour cells and inhibition of tumour cell proliferation. Examples of cancer tumours that may be susceptible to such treatment include, but are not limited to breast cancer and prostate cancer.

In a second aspect of the invention, there is provided the use of a monoclonal antibody to a peptide comprising the N-terminal portion of the angiotensin-II type-1 receptor defined by the sequence (SEQ ID NO: 1)
MILNSSTEDG IKRIQDDCPK AGRHNYIFVM IPTLYSIIFV VGIFG or a fragment thereof, in the preparation of a medicament for the treatment of vascular smooth muscle (VSM) cell proliferation.

Treatment of vascular smooth muscle cell proliferation may include the treatment of atherosclerosis, a complex disease condition that shows an association with VSM cell proliferation.

The first aspect of the invention therefore also extends to a method for the treatment of cancer comprising administration to a subject in need thereof a therapeutic amount of a monoclonal antibody or a fragment thereof to a peptide comprising the N-terminal portion of the angiotensin-II type-1 receptor or a fragment thereof as defined by the amino acid sequences described above.

The second aspect of the invention therefore also extends to a method for the treatment of vascular smooth muscle cell proliferation comprising administration to a subject in need thereof a therapeutic amount of a monoclonal antibody or a fragment thereof to a peptide comprising the N-terminal portion of the angiotensin-II type-1 receptor or a fragment thereof as defined by the amino acid sequence described above.

The antibodies used in accordance with the present invention may be formulated for intravenous injection using appropriate pharmaceutically acceptable adjuvants and/or diluents. Injection may be intravenous, intramuscular, intraperitoneal, including sub-cutaneous injection. Other modes of administration are not excluded, such as for example orally via liposomes, enteric coated capsules and the like.

Suitably, the antibodies used in accordance with the present invention may be humanised antibodies as described in U.S. Pat. No. 4,816,567 and WO 94/10332; or microbodies as described in WO 94/09817; or transgenic antibodies as described in GB-A-2272440. Such synthetic constructs include chimaeric molecules. Thus, for example, uses of humanised (or primatised) antibodies or derivatives thereof are within the scope of the present invention. An example of a humanised antibody is an antibody having human framework regions, but rodent hypervariable regions.

In addition to whole antibodies, the present invention includes uses of derivatives of the monoclonal antibodies defined above which are capable of binding to the epitope selected from the N-terminal region of the angiotensin-II type-1 receptor described above. Thus the present invention also includes uses of antibody fragments. Examples of antibody fragments are given by Dougall et al *Tibtech* 12 372-379 (1994).

Antibody fragments include, for example, Fab, F(ab')$_2$ and Fv fragments (Roitt et al "*Immunology*", Second edition (1989), Churchill Livingstone, London). Fv fragments can be modified to produce a synthetic construct known as a single chain Fv (scFv) molecule. This includes a peptide linker covalently joining $V_h$ and $V_l$ regions which contribute to the stability of the molecule.

Other synthetic constructs include CDR peptides. These are synthetic peptides comprising antigen binding determinants. Peptide mimetics may also be used. These molecules are usually conformationally restricted organic rings which mimic the structure of a CDR loop and which include antigen-interactive side chains. Uses of such molecules able to bind to the desired epitope are therefore also within the scope of the present invention.

In a third aspect of the invention, there is provided the use of a peptide sequence comprising the N-terminal portion of the angiotensin-II type-1 receptor defined by the sequence (SEQ ID NO: 1)
MILNSSTEDG IKRIQDDCPK AGRHNYIFVM IPTLYSIIFV VGIFG or a fragment thereof, in the preparation of a medicament for the treatment of cancer.

In a fourth aspect of the invention there is provided a vaccine composition comprising a peptide sequence comprising the N-terminal portion of the angiotensin-II type-1 receptor defined by the sequence (SEQ ID NO: 1)
MILNSSTEDG IKRIQDDCPK AGRHNYIFVM IPTLYSIIFV VGIFG or a fragment thereof. The vaccine composition may comprise a polypeptide of the above sequence or an antigenic fragment as defined above, optionally conjugated to a carrier protein. Means for rendering such proteins or peptides antigenic are defined above in relation to the earlier aspects of the invention. For example, an albumin protein, such as human serum albumin, bovine serum albumin and ovalbumin. Alternatively, keyhole limpet protein (also sometimes referred to as keyhole limpet haemocyanin) can be used. The carrier will generally be different come from a different species from that on which the fragment is based. Other adjuvants may also be present in the vaccine composition, for example a saponin adjuvant, e.g. a *Quillaja* saponin or a derivative thereof.

In a particularly preferred embodiment there is provided a method for the inhibition of cancer cell growth, adhesion or invasion comprising:
(1) formulating a monoclonal antibody or a fragment thereof to a peptide comprising the N-terminal portion of the angiotensin-II type-1 receptor as defined above, optionally conjugated to a carrier peptide or protein in an appropriate pharmaceutically acceptable adjuvant and/or diluent, such as for intravenous injection
(2) optionally further formulating the monoclonal antibody preparation of (1) as a liposomal or enteric coated capsule formulation
(3) administration of the formulation of (2) or (3) to a population of cancer cells in vitro or a subject suffering from cancer.

Alternatively, this embodiment may also comprise step (1) and (2) only.

Such embodiments extend to the use of such formulations in the preparation of medicaments for the treatment of cancer, for example, prostate cancer, breast cancer (including breast cancer cell adhesion or invasion).

In another preferred embodiment there is provided a method for the inhibition of vascular smooth muscle cell proliferation in which steps (1) to (3) described above are repeated *mutatis mutandis*.

Preferred features for the second and subsequent aspects of the invention are as for the first aspect *mutatis mutandis*.

The invention will now be further described by way of reference to the following Examples which are provided for the purposes of illustration only and are not to be construed as being limiting on the invention.

Example 1

Antibody 6313/G2 Inhibits Cell Proliferation in Prostate PNT1A Cells

The tetrazolium salt, 3-(4,5 dimethylthiazol-2-yl)-2,5-diphenyltetrazolium bromide (MTT) is widely used as an indictor for cellular oxidative metabolic activity. On reduction MTT forms an intensely coloured formazan product, which can be measured colorimetricly and thus is often used for the quantitative assessment of cellular viability and proliferation.

PNT1a, a prostate epithelial cell line were seeded into 96 well culture plate at a concentration of 1000 cells per well. Cells were grown in the presence of RPM I 1640 medium supplemented with 2 mM L-glutamine, 1% non-essential amino acids, 2% penicillin and streptomycin, and 1 mM sodium pyruvate, 10% fetal calf serum, for two days and subsequently rendered quiescent by incubation in RPMI 1640 serum free medium (200 µl/well) for 24 hr. Stimulants were then added at appropriate concentration and incubated for 24 hr and 96 hr. Four hours prior to end of incubation, 20 µl of filtered (0.2 µm pore size) 5 mg/ml solution (in RPMI media) MTT was added to each well and the incubation continued at 37° C. At the appropriate time point, 200 µl of DMSO, followed by 25 µl of Sorensen's glycine buffer (0.1M glycine, 0.1M NaCl adjusted to pH 10.5 with 1M NaOH) was added to each well, mixed thoroughly. After 5 minutes, the absorbance was read at 545 nm.

Results are shown in FIG. 1 in which purified antibody (ab) was added to PNT1a cells in culture. Concentrations of antibody were (1:1600) 100 nmol/l, (1:160) 1 µmol/l, (1:16) 10 µmol/l. Inhibition of proliferation was significant ($P<0.05$ or better) at all concentrations of antibody used.

Example 2

Antibody 6313/G2 Inhibits Cell Proliferation in Vascular Smooth Muscle Cells

ASMCs were isolated from rat thoracic and abdominal artery (RASMC) and bovine aorta (BASMC) by the media explant method and cultured over several passages. Segments of both abdominal and thoracic aortas were obtained from rats by careful dissection from killed rats. Segments of aorta were obtained from calves under anaesthesia. The segments of aorta were placed in a depression slide containing tissue culture medium, after which the adventitia and the outer portion of each segment was carefully removed under a dissecting microscope. The remaining inner portion of the tissue and the intima were removed to a separate dissecting dish and washed several times with fresh culture medium. At this point each segment was cut into approximately 1 mm squares and placed on 25 cm$^2$ tissue culture flask. The flasks were loosely capped and placed in a humidified CO$_2$ incubator. After two hours, 4 ml of RPMI-1640 culture medium supplemented with 100 units/ml of penicillin, 100 µg/ml streptomycin, 4 µmol/L-glutamine and 20% FBS was carefully added to the flasks without dislodging the tissue. Samples were fed with fresh medium after one week. The cells from the explants were relatively confluent within a period of approximately 2 weeks. They were then rinsed with PBS, and subsequently trypsinized with a solution of 0.125% trypsin and 0.02% EDTA in PBS for 1-2 minutes at 37° C. The resulting suspension of cells was pipetted into 75 cm$^2$ tissue culture flasks containing 10 ml culture medium and incubated as above. Experiments were performed with cells from passages 3-5.

A suspension of RASMC ($10^5$ cells/10 were prepared on the first day of the experiment using RPMI-1640 supplemented with 20% FBS. One ml of this cell suspension was distributed to each well of a 24-well multiwell dish. The medium was replaced 24 h after the subculture with RPMI-1640 medium. The quiescent (serum-derived) or serum-replete cells were incubated with the appropriate experimental media for 48 hours 4 wells per group. $^3$H-methylthymidine (0.1 mCi/ml) 10 µl was added to each well (1 ml medium/well). 24 hours after the addition of radioactive thymidine, media were aspirated and the cultured cells were rinsed 3 times with cold PBS. Cells were then dissolved in 0.5 ml of 0.1 N NaOH and a 0.3 ml aliquot was mixed with 3.5 ml of scintillation fluid and, after standing overnight at room temperature, tritium content was assayed in a liquid scintillation counter.

Figure 2:
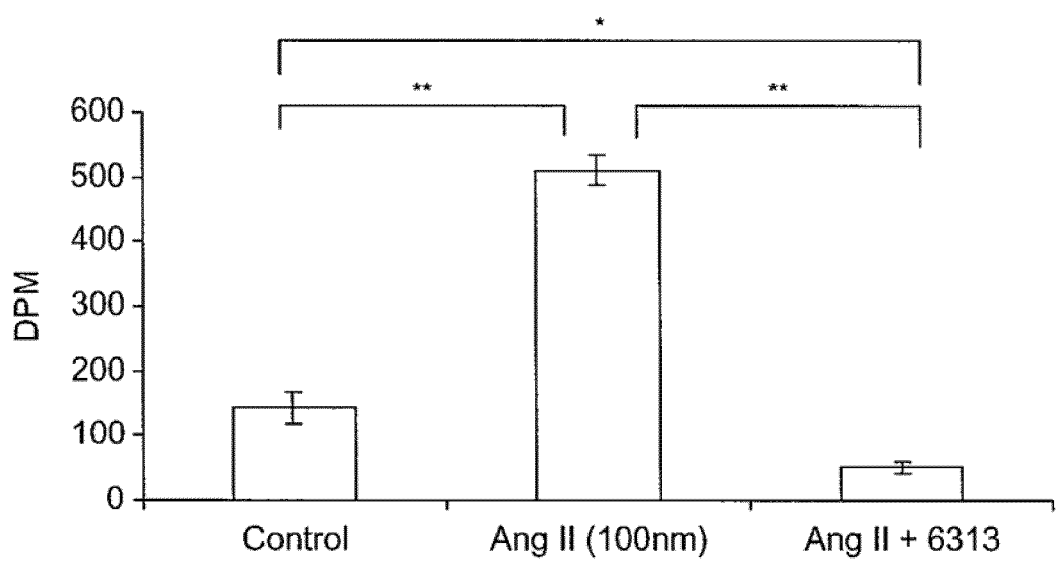
FIG. 2 shows the effects of antibody on aortic smooth muscle cell proliferation by assaying uptake of tritiated thymidine.

Results are shown in FIG. 2 in which proliferation was stimulated by 10 nmol/l angiotensin-II and inhibited by 6313/G2 (10 µmol/L, **P<0.01).

Example 3

Antibody 6313/G2 Inhibits Cell Proliferation in Breast Cancer Cells

MCF-7 cells (obtained from American Type Culture Collection (ATCC) Manassas, Va. 20108, USA) were plated out in 24 well dishes at a density of 5000 cells per well and grown for 24 hours in Eagles's Minimum Essential Medium (MEM) containing 5% fetal bovine serum (FBS). Cells were then incubated for a further 24 hours in serum free medium. Following this, cells were grown in either serum free medium alone (control wells) or serum free medium with addition to experimental wells of angiotensin II alone (1-10 nM), or with antibody 6313/G2. Each treatment was performed in quadruplicate. Cells were then cultured for 24 hours. After 20 hours tritiated thymidine was added to each well (Amersham Pharmacia Biotech, Amersham, UK, 50 µCi/ml, sp. activity 5 Ci/mmol) and cells were cultured for a further 4 hours. At the end of this period the medium was aspirated and the cultured cells were rinsed three times with ice-cold buffer solution (50 mM Tris-HCl, pH 7.4). Cells were then dissolved in 1 ml 0.1N NaOH and 0.5 ml of this solution was mixed with 3.5 ml of scintillation cocktail (toluene scintillator, Packard Bioscience B.V. Groningen, Netherlands) and tritium content was assayed.

Example 4

Antibody 6313 Inhibits Breast Cancer Cell Adhesion

A cell adhesion assay of MCF-7 cells on extracellular matrix protein was carried out to investigate. Cell culture (flat bottomed) 96 well plates were coated with graded amounts of purified human matrix protein, Collagen type IV (50 µg/well). They were left overnight in a laminar flow cabinet to evaporate, at room temperature.

MCF-7 cells (obtained from American Type Culture Collection (ATCC) Manassas, Va. 20108, USA) were treated with 6163/G2 antibody for 48 hours. Controls were untreated. Prior to use, each well was treated with BSA (200 µg/ml) to eliminate non-specific binding.

500 MCF-7 cells in cell culture medium (DMEM) were added to each well and incubated at 37° C. in a 5% $CO_2$ environment for 1 hour. Wells were then washed 3 times with serum-free DMEM and stained with Diff-quick fix (7 seconds), Diff quick I (7 seconds) and Diff quick II (10 seconds) and washed once with water.

Figure 3:
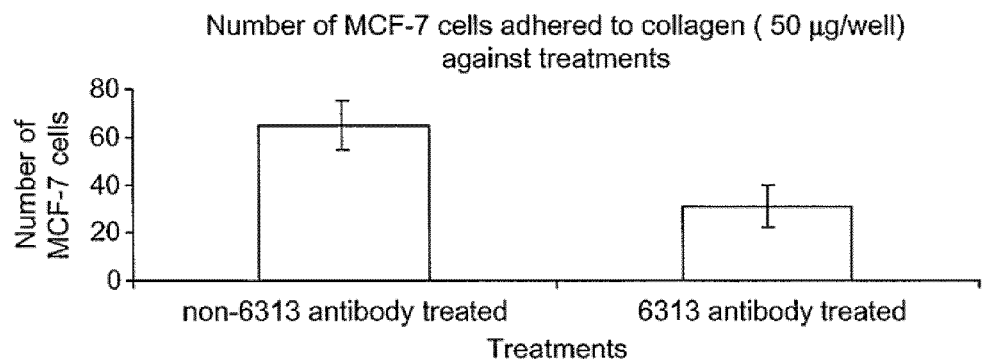
FIG. 3 shows the results of cell adhesion assay of MCF-7 cells on extracellular matrix protein.

Wells were then viewed under a microscope, and the numbers of adhering cells counted. Antibody 6313/G2 significantly reduced cell adhesion (P<0.05). Results are shown in FIG. 3 in which the number of MCF-7 cells adhered to collagen (50 µg/well) against the treatments with and without antibody 6313.

Example 5

Antibody 6313 Inhibits Breast Cancer Cell Invasion

A chemoinvasion assay of MCF-7 cells on extracellular matrix protein was carried out to investigate. 8 µm filter inserts were coated with purified human collagen type IV matrix protein and left overnight in a laminar flow cabinet to dry at room temperature. MCF-7 cells were treated with 6163/G2 antibody (hybridoma supernatant) for 48 hours. Control cells were untreated.

Prior to use, BSA (100 µg/ml) was added to each well for 1 hour. DMEM preconditioned by incubation with 3T3 fibroblast cells was used as the chemoattractant. The coated inserts were placed in each well to form an upper and a lower chamber. 10,000 MCF-7 cells were added into the upper chamber with the addition of serum free DMEM. Conditioned 3T3 cell medium was placed in the lower compartment. Plates were covered and incubated at 37° C. in a humidified 5% $CO_2$ environment for 24 hours.

Figure 4:
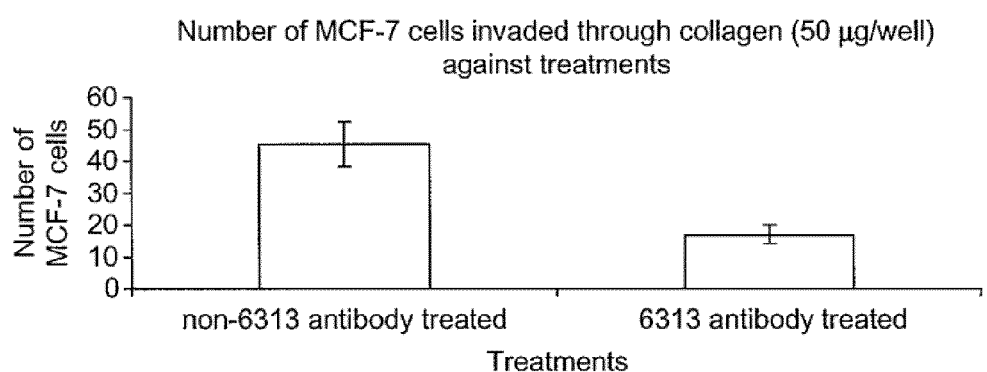
FIG. 4 shows the results of chemoinvasion assay of MCF-7 cells on extracellular matrix protein.

After incubation, the cells remaining on the upper surface of the filter were completely removed and the cells that had traversed the collagen and attached to the lower surface of the filter were stained with Diff-Quik and counted. Results are shown in FIG. 4 in which the number of MCF-7 cells invaded through collagen (50 µu/well) against treatments with and without antibody 6313. Antibody 6313 significantly inhibited cell invasion (P>0.01).

Example 6

Effect of Antibody 6313 on Integrin Expression in Breast Cancer Cells

The effect of antibody 6313/G2 on integrin expression was investigated. The results show that antibody 6313 significantly reduces integrins alpha 3 and beta 1 expression in breast cancer cells.

MCF-7 cell lines was treated for 48 hours with antibody 6313/G2, controls were untreated. Cell membrane fractions were prepared and fractionated non-reduced 8% SDS-PAGE gel.

Figure 5:
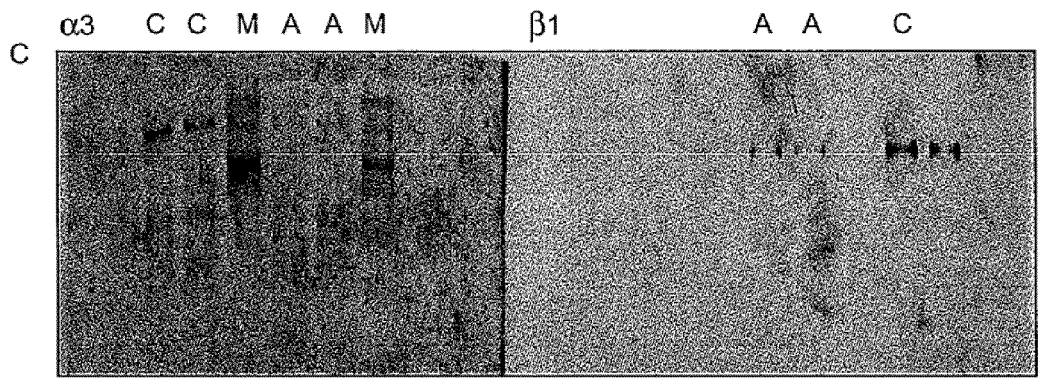
FIG. 5 shows results of Western blots in assay of expression of integrins alpha-3 and beta-1 in breast cancer cells.

Proteins were then transferred to a nitrocellulose membrane overnight, 30V at 4° C. Primary and secondary antibodies for the integrins α3 and β1 were used to detect these components on the nitrocellulose membranes using established methods for Western blotting. Luminescent bands were developed by incubating the membrane in enhanced chemiluminescence (ECL) western blotting detection reagents for 1 minute by hyper film ECL exposure. Results are shown in FIG. 5 in which, C=control, A=antibody tested, other lanes (M) are molecular weight markers.

Example 7

Effect of Antibody 6313 on Calcium Responses in MCF-7 Cells and in RASMC

The effect of antibody 6313 on calcium responses in MCF-7 cells and in RASMC was investigated. Antibody 6313 was found to stimulate the calcium response in both.

For calcium ion ($[Ca^{2+}]$) measurement, the cells were loaded with 1 µM fura-2 for 30 minutes in medium-modified Krebs-Ringer bicarbonate solution (3.6 mM $K^+$, 1.2 mM $Ca^{2+}$, 0.5 mM $Mg^{2+}$, 5 mM Hepes and 20 mM $HCO^-$) at 37° C. For simultaneous measurements of measuring the fluorescence of fura-2, the cells plated on coverslips were mounted on the stage of an inverted microscope (Zeiss) in a modified Krebs-Ringer bicarbonate solution. The excitation wavelengths were 340 nm and 380 nm, and emission was detected at 510 nm. Calcium ion concentration ($[Ca^{2+}]$) was calculated from the ration of fluorescence intensities at excitation wavelengths of 340 nm and 380 nm.

Figure 6:
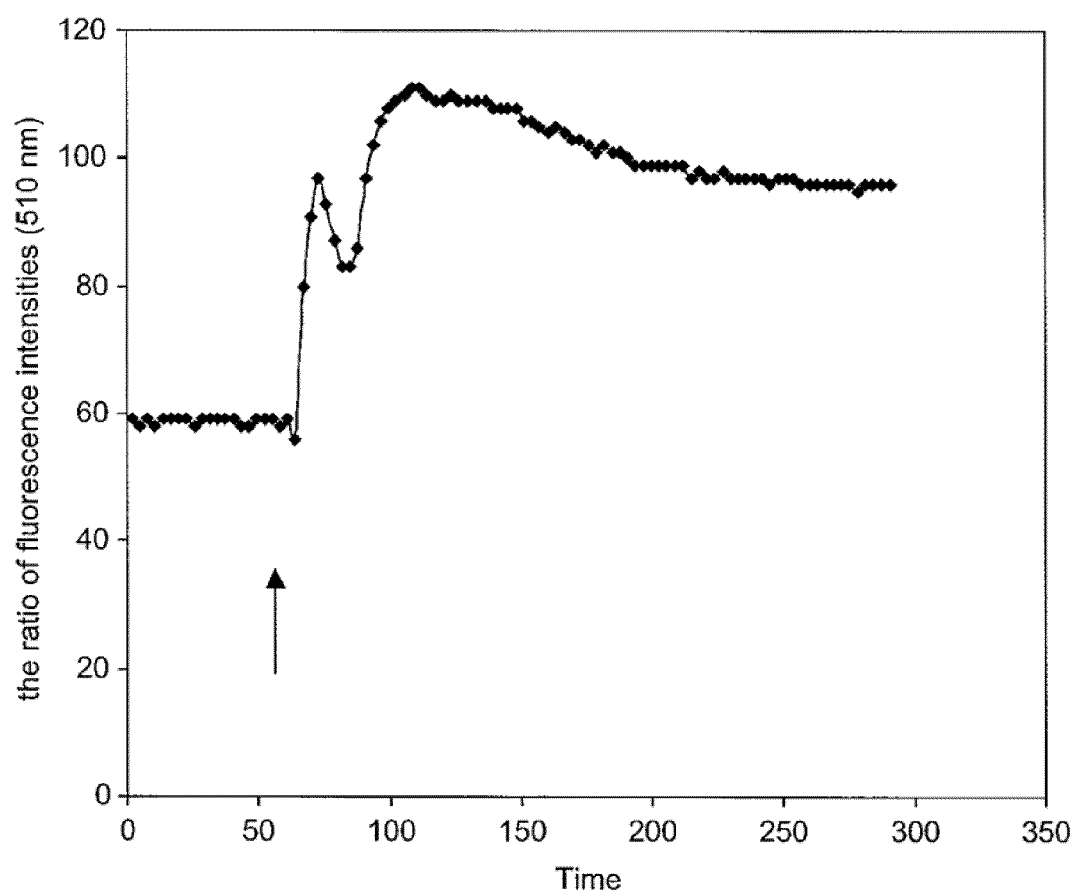
FIG. 6 shows antibody 6313/G2 stimulation of calcium responses in MCF-7 cells.
Figure 7:
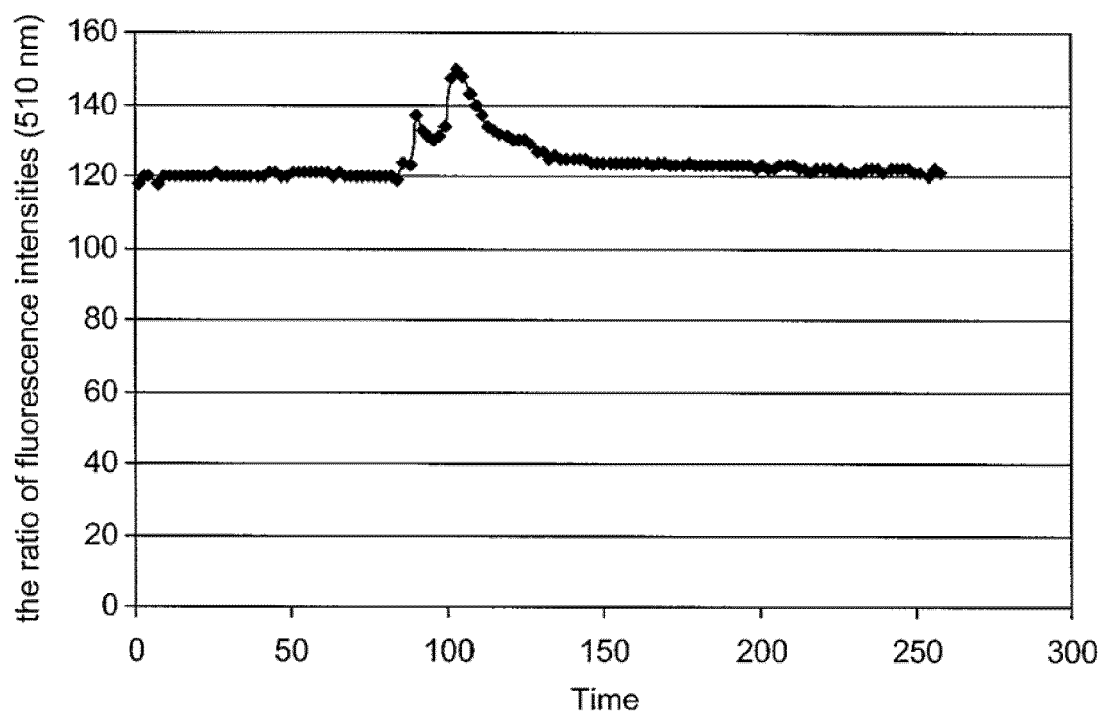
FIG. 7 shows antibody 6313/G2 stimulation of calcium responses in RASMC.
Figure 8:
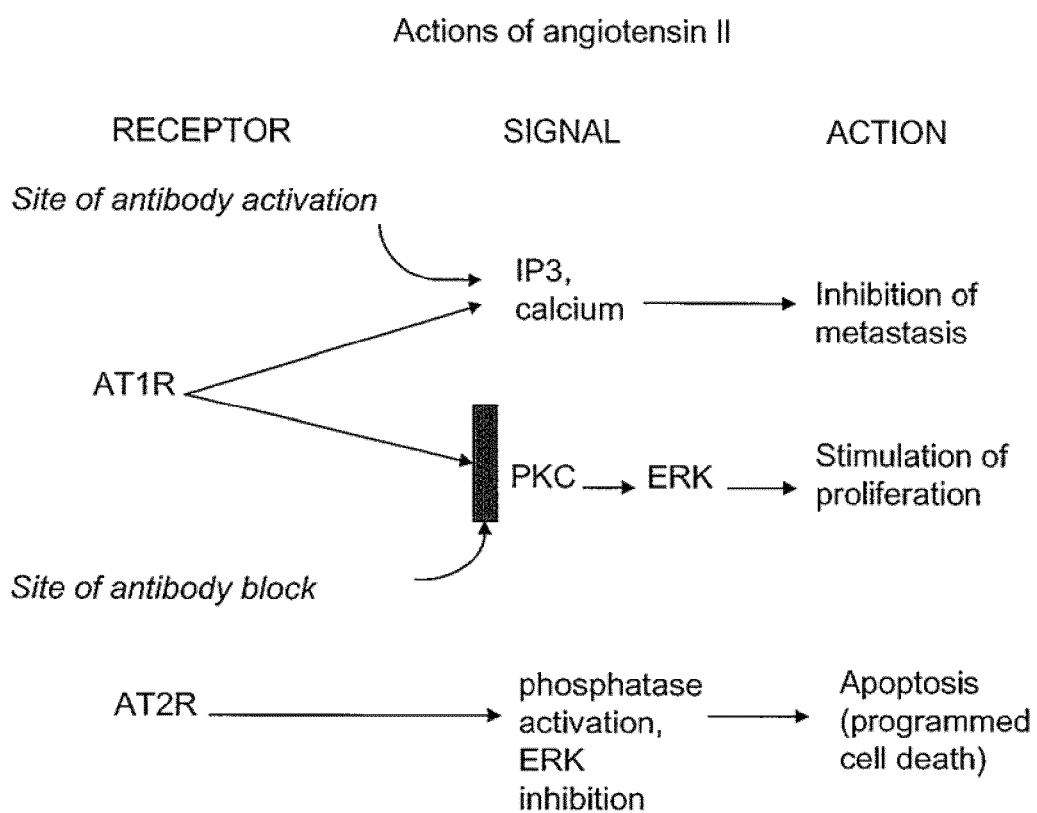
FIG. 8 shows a schematic diagram of the actions of angiotensin-II, the site of the monoclonal antibody activation and the site of monoclonal antibody block.

Results are shown in FIG. 6 in MCF-7 cells and in RASMC. The vertical arrow indicates the point of application if antibody 6313/G2. The increased ration of fluorescence intensities is proportional to the intracellular calcium ion concentration.

The invention claimed is:

1. A method of treating cancer comprising administering to a subject in need thereof a therapeutically effective amount of a monoclonal antibody, or an antigen binding fragment thereof, that binds to a peptide consisting of the sequence EDGIKRIQDD (SEQ ID NO: 2).

2. The method of claim 1 wherein the monoclonal antibody is humanized.

3. The method of claim 1 wherein the antigen binding fragment is a Fab, F(ab')$_2$, Fv, or scFv.

4. The method of claim 1 wherein the cancer is prostate cancer or breast cancer.

* * * * *

SEQUENCE LISTING

<160> NUMBER OF SEQ ID NOS: 72

<210> SEQ ID NO 1
<211> LENGTH: 45
<212> TYPE: PRT
<213> ORGANISM: Homo sapiens

<400> SEQUENCE: 1

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
            20                  25                  30

Thr Leu Tyr Ser Ile Ile Phe Val Val Gly Ile Phe Gly
        35                  40                  45

<210> SEQ ID NO 2
<211> LENGTH: 10
<212> TYPE: PRT
<213> ORGANISM: Homo sapiens

<400> SEQUENCE: 2

Glu Asp Gly Ile Lys Arg Ile Gln Asp Asp
1               5                   10

<210> SEQ ID NO 3
<211> LENGTH: 5
<212> TYPE: PRT
<213> ORGANISM: Homo sapiens

<400> SEQUENCE: 3

Thr Glu Asp Gly Ile
1               5

<210> SEQ ID NO 4
<211> LENGTH: 5
<212> TYPE: PRT
<213> ORGANISM: Homo sapiens

<400> SEQUENCE: 4

Glu Asp Gly Ile Lys
1               5

<210> SEQ ID NO 5
<211> LENGTH: 5
<212> TYPE: PRT
<213> ORGANISM: Homo sapiens

<400> SEQUENCE: 5

Asp Gly Ile Lys Arg
1               5

<210> SEQ ID NO 6
<211> LENGTH: 5
<212> TYPE: PRT
<213> ORGANISM: Homo sapiens

<400> SEQUENCE: 6

Gly Ile Lys Arg Ile
1               5

<210> SEQ ID NO 7
<211> LENGTH: 5
<212> TYPE: PRT

```
<213> ORGANISM: Homo sapiens

<400> SEQUENCE: 7

Ile Lys Arg Ile Gln
1               5

<210> SEQ ID NO 8
<211> LENGTH: 5
<212> TYPE: PRT
<213> ORGANISM: Homo sapiens

<400> SEQUENCE: 8

Lys Arg Ile Gln Asp
1               5

<210> SEQ ID NO 9
<211> LENGTH: 5
<212> TYPE: PRT
<213> ORGANISM: Homo sapiens

<400> SEQUENCE: 9

Arg Ile Gln Asp Asp
1               5

<210> SEQ ID NO 10
<211> LENGTH: 5
<212> TYPE: PRT
<213> ORGANISM: Homo sapiens

<400> SEQUENCE: 10

Ile Gln Asp Asp Cys
1               5

<210> SEQ ID NO 11
<211> LENGTH: 6
<212> TYPE: PRT
<213> ORGANISM: Homo sapiens

<400> SEQUENCE: 11

Ser Thr Glu Asp Gly Ile
1               5

<210> SEQ ID NO 12
<211> LENGTH: 6
<212> TYPE: PRT
<213> ORGANISM: Homo sapiens

<400> SEQUENCE: 12

Thr Glu Asp Gly Ile Lys
1               5

<210> SEQ ID NO 13
<211> LENGTH: 6
<212> TYPE: PRT
<213> ORGANISM: Homo sapiens

<400> SEQUENCE: 13

Glu Asp Gly Ile Lys Arg
1               5

<210> SEQ ID NO 14
<211> LENGTH: 6
<212> TYPE: PRT
<213> ORGANISM: Homo sapiens

<400> SEQUENCE: 14
```

```
Asp Gly Ile Lys Arg Ile
1               5

<210> SEQ ID NO 15
<211> LENGTH: 6
<212> TYPE: PRT
<213> ORGANISM: Homo sapiens

<400> SEQUENCE: 15

Gly Ile Lys Arg Ile Gln
1               5

<210> SEQ ID NO 16
<211> LENGTH: 6
<212> TYPE: PRT
<213> ORGANISM: Homo sapiens

<400> SEQUENCE: 16

Ile Lys Arg Ile Gln Asp
1               5

<210> SEQ ID NO 17
<211> LENGTH: 6
<212> TYPE: PRT
<213> ORGANISM: Homo sapiens

<400> SEQUENCE: 17

Lys Arg Ile Gln Asp Asp
1               5

<210> SEQ ID NO 18
<211> LENGTH: 6
<212> TYPE: PRT
<213> ORGANISM: Homo sapiens

<400> SEQUENCE: 18

Arg Ile Gln Asp Asp Cys
1               5

<210> SEQ ID NO 19
<211> LENGTH: 6
<212> TYPE: PRT
<213> ORGANISM: Homo sapiens

<400> SEQUENCE: 19

Ile Gln Asp Asp Cys Pro
1               5

<210> SEQ ID NO 20
<211> LENGTH: 7
<212> TYPE: PRT
<213> ORGANISM: Homo sapiens

<400> SEQUENCE: 20

Ser Ser Thr Glu Asp Gly Ile
1               5

<210> SEQ ID NO 21
<211> LENGTH: 7
<212> TYPE: PRT
<213> ORGANISM: Homo sapiens

<400> SEQUENCE: 21

Ser Thr Glu Asp Gly Ile Lys
1               5
```

<210> SEQ ID NO 22
<211> LENGTH: 7
<212> TYPE: PRT
<213> ORGANISM: Homo sapiens

<400> SEQUENCE: 22

Thr Glu Asp Gly Ile Lys Arg
1               5

<210> SEQ ID NO 23
<211> LENGTH: 7
<212> TYPE: PRT
<213> ORGANISM: Homo sapiens

<400> SEQUENCE: 23

Glu Asp Gly Ile Lys Arg Ile
1               5

<210> SEQ ID NO 24
<211> LENGTH: 7
<212> TYPE: PRT
<213> ORGANISM: Homo sapiens

<400> SEQUENCE: 24

Asp Gly Ile Lys Arg Ile Gln
1               5

<210> SEQ ID NO 25
<211> LENGTH: 7
<212> TYPE: PRT
<213> ORGANISM: Homo sapiens

<400> SEQUENCE: 25

Gly Ile Lys Arg Ile Gln Asp
1               5

<210> SEQ ID NO 26
<211> LENGTH: 7
<212> TYPE: PRT
<213> ORGANISM: Homo sapiens

<400> SEQUENCE: 26

Ile Lys Arg Ile Gln Asp Asp
1               5

<210> SEQ ID NO 27
<211> LENGTH: 7
<212> TYPE: PRT
<213> ORGANISM: Homo sapiens

<400> SEQUENCE: 27

Lys Arg Ile Gln Asp Asp Cys
1               5

<210> SEQ ID NO 28
<211> LENGTH: 7
<212> TYPE: PRT
<213> ORGANISM: Homo sapiens

<400> SEQUENCE: 28

Arg Ile Gln Asp Asp Cys Pro
1               5

<210> SEQ ID NO 29

```
<211> LENGTH: 7
<212> TYPE: PRT
<213> ORGANISM: Homo sapiens

<400> SEQUENCE: 29

Ile Gln Asp Asp Cys Pro Lys
1               5

<210> SEQ ID NO 30
<211> LENGTH: 8
<212> TYPE: PRT
<213> ORGANISM: Homo sapiens

<400> SEQUENCE: 30

Asn Ser Ser Thr Glu Asp Gly Ile
1               5

<210> SEQ ID NO 31
<211> LENGTH: 8
<212> TYPE: PRT
<213> ORGANISM: Homo sapiens

<400> SEQUENCE: 31

Ser Ser Thr Glu Asp Gly Ile Lys
1               5

<210> SEQ ID NO 32
<211> LENGTH: 8
<212> TYPE: PRT
<213> ORGANISM: Homo sapiens

<400> SEQUENCE: 32

Ser Thr Glu Asp Gly Ile Lys Arg
1               5

<210> SEQ ID NO 33
<211> LENGTH: 8
<212> TYPE: PRT
<213> ORGANISM: Homo sapiens

<400> SEQUENCE: 33

Thr Glu Asp Gly Ile Lys Arg Ile
1               5

<210> SEQ ID NO 34
<211> LENGTH: 8
<212> TYPE: PRT
<213> ORGANISM: Homo sapiens

<400> SEQUENCE: 34

Glu Asp Gly Ile Lys Arg Ile Gln
1               5

<210> SEQ ID NO 35
<211> LENGTH: 8
<212> TYPE: PRT
<213> ORGANISM: Homo sapiens

<400> SEQUENCE: 35

Asp Gly Ile Lys Arg Ile Gln Asp
1               5

<210> SEQ ID NO 36
<211> LENGTH: 8
<212> TYPE: PRT
<213> ORGANISM: Homo sapiens
```

-continued

<400> SEQUENCE: 36

Gly Ile Lys Arg Ile Gln Asp Asp
1               5

<210> SEQ ID NO 37
<211> LENGTH: 8
<212> TYPE: PRT
<213> ORGANISM: Homo sapiens

<400> SEQUENCE: 37

Ile Lys Arg Ile Gln Asp Asp Cys
1               5

<210> SEQ ID NO 38
<211> LENGTH: 8
<212> TYPE: PRT
<213> ORGANISM: Homo sapiens

<400> SEQUENCE: 38

Lys Arg Ile Gln Asp Asp Cys Pro
1               5

<210> SEQ ID NO 39
<211> LENGTH: 8
<212> TYPE: PRT
<213> ORGANISM: Homo sapiens

<400> SEQUENCE: 39

Arg Ile Gln Asp Asp Cys Pro Lys
1               5

<210> SEQ ID NO 40
<211> LENGTH: 8
<212> TYPE: PRT
<213> ORGANISM: Homo sapiens

<400> SEQUENCE: 40

Ile Gln Asp Asp Cys Pro Lys Ala
1               5

<210> SEQ ID NO 41
<211> LENGTH: 9
<212> TYPE: PRT
<213> ORGANISM: Homo sapiens

<400> SEQUENCE: 41

Leu Asn Ser Ser Thr Glu Asp Gly Ile
1               5

<210> SEQ ID NO 42
<211> LENGTH: 9
<212> TYPE: PRT
<213> ORGANISM: Homo sapiens

<400> SEQUENCE: 42

Asn Ser Ser Thr Glu Asp Gly Ile Lys
1               5

<210> SEQ ID NO 43
<211> LENGTH: 9
<212> TYPE: PRT
<213> ORGANISM: Homo sapiens

<400> SEQUENCE: 43

```
Ser Ser Thr Glu Asp Gly Ile Lys Arg
1               5
```

<210> SEQ ID NO 44
<211> LENGTH: 9
<212> TYPE: PRT
<213> ORGANISM: Homo sapiens

<400> SEQUENCE: 44

```
Ser Thr Glu Asp Gly Ile Lys Arg Ile
1               5
```

<210> SEQ ID NO 45
<211> LENGTH: 9
<212> TYPE: PRT
<213> ORGANISM: Homo sapiens

<400> SEQUENCE: 45

```
Thr Glu Asp Gly Ile Lys Arg Ile Gln
1               5
```

<210> SEQ ID NO 46
<211> LENGTH: 9
<212> TYPE: PRT
<213> ORGANISM: Homo sapiens

<400> SEQUENCE: 46

```
Glu Asp Gly Ile Lys Arg Ile Gln Asp
1               5
```

<210> SEQ ID NO 47
<211> LENGTH: 9
<212> TYPE: PRT
<213> ORGANISM: Homo sapiens

<400> SEQUENCE: 47

```
Asp Gly Ile Lys Arg Ile Gln Asp Asp
1               5
```

<210> SEQ ID NO 48
<211> LENGTH: 9
<212> TYPE: PRT
<213> ORGANISM: Homo sapiens

<400> SEQUENCE: 48

```
Gly Ile Lys Arg Ile Gln Asp Asp Cys
1               5
```

<210> SEQ ID NO 49
<211> LENGTH: 9
<212> TYPE: PRT
<213> ORGANISM: Homo sapiens

<400> SEQUENCE: 49

```
Ile Lys Arg Ile Gln Asp Asp Cys Pro
1               5
```

<210> SEQ ID NO 50
<211> LENGTH: 9
<212> TYPE: PRT
<213> ORGANISM: Homo sapiens

<400> SEQUENCE: 50

```
Lys Arg Ile Gln Asp Asp Cys Pro Lys
1               5
```

<210> SEQ ID NO 51
<211> LENGTH: 9
<212> TYPE: PRT
<213> ORGANISM: Homo sapiens

<400> SEQUENCE: 51

Arg Ile Gln Asp Asp Cys Pro Lys Ala
1               5

<210> SEQ ID NO 52
<211> LENGTH: 9
<212> TYPE: PRT
<213> ORGANISM: Homo sapiens

<400> SEQUENCE: 52

Ile Gln Asp Asp Cys Pro Lys Ala Gly
1               5

<210> SEQ ID NO 53
<211> LENGTH: 10
<212> TYPE: PRT
<213> ORGANISM: Homo sapiens

<400> SEQUENCE: 53

Ile Leu Asn Ser Ser Thr Glu Asp Gly Ile
1               5                   10

<210> SEQ ID NO 54
<211> LENGTH: 10
<212> TYPE: PRT
<213> ORGANISM: Homo sapiens

<400> SEQUENCE: 54

Leu Asn Ser Ser Thr Glu Asp Gly Ile Lys
1               5                   10

<210> SEQ ID NO 55
<211> LENGTH: 10
<212> TYPE: PRT
<213> ORGANISM: Homo sapiens

<400> SEQUENCE: 55

Asn Ser Ser Thr Glu Asp Gly Ile Lys Arg
1               5                   10

<210> SEQ ID NO 56
<211> LENGTH: 10
<212> TYPE: PRT
<213> ORGANISM: Homo sapiens

<400> SEQUENCE: 56

Ser Ser Thr Glu Asp Gly Ile Lys Arg Ile
1               5                   10

<210> SEQ ID NO 57
<211> LENGTH: 10
<212> TYPE: PRT
<213> ORGANISM: Homo sapiens

<400> SEQUENCE: 57

Ser Thr Glu Asp Gly Ile Lys Arg Ile Gln
1               5                   10

<210> SEQ ID NO 58
<211> LENGTH: 10

```
<212> TYPE: PRT
<213> ORGANISM: Homo sapiens

<400> SEQUENCE: 58

Thr Glu Asp Gly Ile Lys Arg Ile Gln Asp
1               5                   10

<210> SEQ ID NO 59
<211> LENGTH: 10
<212> TYPE: PRT
<213> ORGANISM: Homo sapiens

<400> SEQUENCE: 59

Glu Asp Gly Ile Lys Arg Ile Gln Asp Asp
1               5                   10

<210> SEQ ID NO 60
<211> LENGTH: 10
<212> TYPE: PRT
<213> ORGANISM: Homo sapiens

<400> SEQUENCE: 60

Asp Gly Ile Lys Arg Ile Gln Asp Asp Cys
1               5                   10

<210> SEQ ID NO 61
<211> LENGTH: 10
<212> TYPE: PRT
<213> ORGANISM: Homo sapiens

<400> SEQUENCE: 61

Gly Ile Lys Arg Ile Gln Asp Asp Cys Pro
1               5                   10

<210> SEQ ID NO 62
<211> LENGTH: 10
<212> TYPE: PRT
<213> ORGANISM: Homo sapiens

<400> SEQUENCE: 62

Ile Lys Arg Ile Gln Asp Asp Cys Pro Lys
1               5                   10

<210> SEQ ID NO 63
<211> LENGTH: 10
<212> TYPE: PRT
<213> ORGANISM: Homo sapiens

<400> SEQUENCE: 63

Lys Arg Ile Gln Asp Asp Cys Pro Lys Ala
1               5                   10

<210> SEQ ID NO 64
<211> LENGTH: 10
<212> TYPE: PRT
<213> ORGANISM: Homo sapiens

<400> SEQUENCE: 64

Arg Ile Gln Asp Asp Cys Pro Lys Ala Gly
1               5                   10

<210> SEQ ID NO 65
<211> LENGTH: 10
<212> TYPE: PRT
<213> ORGANISM: Homo sapiens
```

```
<400> SEQUENCE: 65

Ile Gln Asp Asp Cys Pro Lys Ala Gly Arg
1               5                   10

<210> SEQ ID NO 66
<211> LENGTH: 45
<212> TYPE: PRT
<213> ORGANISM: Bos sp.

<400> SEQUENCE: 66

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Ile Met Ile Pro
                20                  25                  30

Thr Leu Tyr Ser Ile Ile Phe Val Val Gly Ile Phe Gly
            35                  40                  45

<210> SEQ ID NO 67
<211> LENGTH: 45
<212> TYPE: PRT
<213> ORGANISM: Ovis sp.

<400> SEQUENCE: 67

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Ile Met Ile Pro
                20                  25                  30

Thr Leu Tyr Ser Ile Ile Phe Val Val Gly Leu Phe Gly
            35                  40                  45

<210> SEQ ID NO 68
<211> LENGTH: 45
<212> TYPE: PRT
<213> ORGANISM: Oryctolagus cuniculus

<400> SEQUENCE: 68

Met Met Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
                20                  25                  30

Thr Leu Tyr Ser Ile Ile Phe Val Val Gly Ile Phe Gly
            35                  40                  45

<210> SEQ ID NO 69
<211> LENGTH: 45
<212> TYPE: PRT
<213> ORGANISM: Rattus sp.

<400> SEQUENCE: 69

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
                20                  25                  30

Thr Leu Tyr Ser Ile Ile Phe Met Val Gly Ile Phe Gly
            35                  40                  45

<210> SEQ ID NO 70
<211> LENGTH: 44
<212> TYPE: PRT
<213> ORGANISM: Cavia porcellus

<400> SEQUENCE: 70
```

```
Met Ile Leu Asn Ser Ser Thr Gln Asp Gly Ile Lys Arg Ile Gln Asp
1               5                   10                  15

Asp Cys Pro Lys Gly Arg His Ser Tyr Ile Phe Val Met Ile Pro Thr
                20                  25                  30

Leu Tyr Ser Ile Ile Phe Val Val Gly Ile Phe Gly
            35                  40

<210> SEQ ID NO 71
<211> LENGTH: 43
<212> TYPE: PRT
<213> ORGANISM: Rattus sp.

<400> SEQUENCE: 71

Met Leu Asn Ser Ser Asp Asp Gly Ile Lys Arg Ile Gln Asp Cys
1               5                   10                  15

Pro Lys Ala Gly Arg His Ser Tyr Ile Phe Val Met Ile Pro Thr Leu
                20                  25                  30

Tyr Ser Ile Ile Phe Val Val Gly Ile Phe Gly
            35                  40

<210> SEQ ID NO 72
<211> LENGTH: 42
<212> TYPE: PRT
<213> ORGANISM: Mus musculus

<400> SEQUENCE: 72

Met Leu Asn Ser Ser Glu Asp Gly Ile Lys Arg Ile Gln Asp Cys
1               5                   10                  15

Pro Ser Gly Arg His Ser Tyr Ile Phe Val Met Ile Pro Thr Leu Tyr
                20                  25                  30

Ser Ile Met Phe Val Val Gly Ile Phe Gly
            35                  40
```